United States Patent [19]

Gaffar

[11] Patent Number: 5,260,062
[45] Date of Patent: Nov. 9, 1993

[54] ANTI-PLAQUE AND ANTI-TARTAR DENTIFRICES IN PLASTIC PUMP DISPENSERS

[75] Inventor: Abdul Gaffar, Princeton, N.J.

[73] Assignee: Colgate-Palmolive Company, Piscataway, N.J.

[21] Appl. No.: 547,641

[22] Filed: Jul. 2, 1990

Related U.S. Application Data

[63] Continuation-in-part of Ser. No. 505,628, Apr. 6, 1990, Pat. No. 5,167,951, which is a continuation of Ser. No. 427,660, Oct. 26, 1989, Pat. No. 5,135,738, which is a continuation-in-part of Ser. No. 398,566, Aug. 25, 1989, Pat. No. 5,032,386, and a continuation-in-part of Ser. No. 398,592, Aug. 28, 1989, abandoned, and a continuation-in-part of Ser. No. 398,605, Aug. 25, 1989, abandoned, and a continuation-in-part of Ser. No. 398,606, Aug. 25, 1989, abandoned, and a continuation-in-part of Ser. No. 399,669, Aug. 25, 1989, abandoned, and a continuation-in-part of Ser. No. 410,682, Sep. 21, 1989, abandoned, said Ser. No. 410,682, is a continuation-in-part of Ser. No. 291,712, Dec. 29, 1988, Pat. No. 4,894,220.

[51] Int. Cl.⁵ ............................ A61K 7/16; A61K 7/18
[52] U.S. Cl. ................................ 424/401; 424/49; 424/52; 424/57; 206/277; 206/524.1; 206/524.3; 206/524.4; 222/106; 222/107; 222/251; 222/256; 514/970
[58] Field of Search .............. 424/49, 52, 57, 401; 206/277, 524.1, 524.3, 524.4; 222/106, 107, 251, 256; 514/970

[56] References Cited

U.S. PATENT DOCUMENTS

| | | | |
|---|---|---|---|
| 4,830,221 | 5/1989 | Mazzanobile | 424/49 |
| 4,933,171 | 6/1990 | Bristow et al. | 424/49 |
| 4,933,173 | 6/1990 | Bristow et al. | 424/49 |
| 4,980,153 | 12/1990 | Jackson et al. | 424/49 |
| 4,988,499 | 1/1991 | Bristow et al. | 424/52 |
| 5,019,373 | 5/1991 | Carter et al. | 424/49 |
| 5,026,539 | 6/1991 | Jackson et al. | 424/49 |
| 5,032,385 | 7/1991 | Reed et al. | 424/49 |
| 5,135,738 | 8/1992 | Gaffar et al. | 424/49 |

Primary Examiner—Shep K. Rose
Attorney, Agent, or Firm—Robert L. Stone; Murray M. Grill; Robert C. Sullivan

[57] ABSTRACT

A dental composition, such as a paste or gel dentifrice containing triclosan, as an antibacterial agent which acts to decrease plaque on the teeth, and polyphosphate for anti-tartar actions, is packaged in a finger actuatable pump-type plastic dispensing container which is made of or includes a solid polymeric material, such as a polyfluoroethylene, which is compatible with triclosan, so that excessive loss of its anti-plaque activity on storage is avoided, which losses have been noted when various other plastics have been employed as dispensing container component materials. Alternatively, others of such plastic may be employed for dispensing container parts when a stabilizer, such as a terpene, e.g., limonene, is present in the dentifrice. The dentifrice preferably also contains a tooth hardening propotion of a source of fluoride ions, a stabilizing proportion (in conjunction with the fluoride source) for the polyphosphate, of a polyvinyl methyl ether-maleic anhydride copolymer, and normal dentifrice adjuvants.

20 Claims, 1 Drawing Sheet

ANTI-PLAQUE AND ANTI-TARTAR DENTIFRICES IN PLASTIC PUMP DISPENSERS

This application is a continuation-in-part of U.S. patent application Ser. No. 07/505,628, filed Apr. 6, 1990 (now U.S. Pat. No. 5,167,951, granted Dec. 1, 1992), which is a continuation of U.S. patent application Ser. No. 07/427,660, filed Oct. 26, 1989 (now U.S. Pat. No. 5,135,738 granted Aug. 4, 1992), which is a continuation-in-part of each of U.S. patent applications Ser. Nos. 07/398,566, now U.S. Pat. No. 5,032,386, granted Jul. 16, 1991; 07/398,605, 07/398,606 and 07/399,669, each now abandoned, all of which were filed on Aug. 25, 1989, Ser. No. 07/398,592, filed Aug. 28, 1989, and of Ser. No. 410,682, filed Sep. 21, 1989, Ser. No. 07/399,592, filed Aug. 28, 1989, all of which are continuations-in-part of Ser. No. 07/291,712, filed Dec. 29, 1988 and now U.S. Pat. No. 4,894,220 granted Jan. 16, 1990.

This invention relates to packaged anti-plaque dental compositions which comprise an antibacterial agent, triclosan (THDE, 2',4,4'-trichloro-2-hydroxydiphenylether), as an effective anti-plaque component, and polyphosphate as an effective anti-tartar component which compositions are packaged in a pump-type dispensing container which includes a polymeric plastic material in contact with the oral composition, which plastic is compatible with the triclosan in the composition.

Although various plastics may diminish the anti-plaque action of triclosan, certain plastics, such as polyfluoroethylene and polyvinyl chloride, have been found to be compatible with triclosan and it has been discovered that they do not cause excessive losses of antibacterial and anti-plaque activities of dentifrices contacting them during storage at room temperature and even at elevated temperatures. Also, applicant has discovered that when contacting parts of the container are of a plastic which is not in itself entirely compatible with triclosan compatibility can be improved by incorporating in the dentifrice formula a stabilizing proportion of a material discovered by applicant to have stabilizing properties, such as a terpene, e.g., limonene, or an essential oil (natural or synthetic), which may be a component of a flavoring material for the dentifrice, and thereby can perform a dual function in the packaged dentifrice. Such stabilizer is present in sufficient proportion so that the dentifrice, as packaged and dispensed, is effective in anti-plaque action, which is a major object of this invention.

The packaged dentifrices of the invention preferably include in the dentifrice compositions fluoride or a source of fluoride ions for tooth hardening and anti-caries actions, and polyvinyl methyl ether/maleic anhydride copolymer, which, in conjunction with the fluoride, stabilizes the polyphosphate anti-tartar agent and improves the anti-plaque action of triclosan.

Plaque on teeth is considered to be a causative factor of negative periodontal conditions, and dental plaque is a precursor of calculi. Plaque may form on any part of the tooth surface, including the gingival margin. It makes the teeth appear dull and in addition to promoting development of calculi, it has been implicated in occurrences of gingivitis. Therefore, dentifrices that contain anti-plaque components which prevent or inhibit the development of plaque on the teeth are valuable dental care aids. Tartar or dental calculus is also known to be causative of gingivitis and dental decay, and makes the teeth appear dull and unattractive. Although it has been known that antimicrobial agents in dentifrices may reduce plaque, various other antibacterial compounds than triclosan often are of disadvantageous characteristics which contraindicate their employment in such oral compositions. For example, cationic antibacterial compounds, such as quaternary ammonium halides, tend to discolor the teeth and may be inactivated by the presence of anionic materials in the dentifrices (and often it will be desirable to employ anionic surfactants or detergents in dentifrices). Triclosan can be inactivated by nonionic surfactants and by various plastics, as has been discovered by applicant, Thus, an object of this invention has been to incorporate triclosan and similar compounds, such as DDDE (2,2'-dihydroxy-5,5'-dibromo-diphenyl ether), in dentifrices for their anti-plaque activity and to store such dentifrices in and dispense them from packages or containers in which they will not lose an excessive proportion of such activity on storage, before intended use, or during dispensing. In prior art triclosan dentifrices, as delivered from the dispenser, the triclosan delivery has not been in an effective amount to significantly reduce plaque when employed once or twice daily at 1.5 grams of dentifrice in one minute brushings, which is considered to approximate normal brushing practice. To be effective, such uses should result in at least a 25% reduction in plaque after three weeks' use, compared to similar usage of a control toothpaste.

Triclosan is described in U.S. Pat. No. 4,022,880 as an antibacterial agent in combination with an anti-calculus agent (which provides zinc ions), and it is disclosed in German patent specification (OLS) No. 35 32 860 in combination with a copper compound. It is also mentioned in European patent applications No's. 0 161 989 and 0 161 899, and in European patent application No. 0 220 890 it is disclosed in dentifrices with polyethylene glycol and oil based flavor.

Various types of dentifrices are known, including paste, gel, powder, liquid, tablet, lozenge, sachet and packeted dentifrices. Such products have been packed in deformable tubes, pressurized dispensers, packets, bottles, jars and other containers, including pump dispensers. In recent years such containers have often been made of synthetic organic polymeric plastics or of laminates which include such plastics, and plastic pump dispensers are now utilized in toothpaste packages that are marketed. Interactions between dentifrices and the materials of containers in which they were packed have been known, such as reaction between toothpastes and aluminum containers, and to prevent such reactions containers have been especially treated or different container materials have been employed. However, applicant does not believe that before this invention it had been known to the prior art that plastic pump dispenser materials of construction could adversely affect the anti-plaque activities of triclosan (and DDDE and similar anti-plaque agents) that had been incorporated in such dispensers, in which they came into contact with such plastics, nor does he believe that it had been discovered that certain plastics could be employed for such container parts without causing losses of the anti-plaque activities of triclosan and related halogenated diphenyl ethers (triclosan only will be referred to later herein, for simplicity) or that losses of such anti-plaque activity of dentifrices packed in dispensers in contact with "reactive" plastics (which react with, absorb or otherwise reduce the anti-plaque activity of the dentifrice) could be inhibited or prevented by incorporation in the dentifrices of terpenes, such as limonene, and other stabilizing components of flavoring materials.

Polyphosphates, which are anti-tartar components of the invented packaged dentifrices, tooth hardening and stabilizing fluoride or other source of fluorine ions, and polymeric polycarboxylate, such as the polyvinyl methyl ether/maleic anhydride copolymers, which can increase the effectivenesses of the polyphosphate and fluoride, and act to inhibit development of calculi, are dental preparation components that are known to the art. U.S. patent application Ser. No. 07/398,772, filed Aug. 25, 1989, U.S. Pat. Nos. 4,323,551, 4,515,772 and 4,627,977, and European patent application 89 200 710.5 are considered to be of relevance to such aspects of the present invention.

Hand holdable pump dispensers for viscous materials, which are the preferred dispensing containers for the dentifrices in accordance with the invention are described in U.S. Pat. Nos. 4,684,044 and 4,691,847 (Realex Corporation) and in U.S. Pat. No. 4,776,496 (Guala S.p.A.). The pump dispensers illustrated in those patents are of the finger actuated, floating piston type.

In accordance with the present invention a dispensing container of a viscous anti-plaque and anti-tartar dentifrice comprises such a dentifrice, which comprises an effective anti-plaque proportion of triclosan and an effective anti-tartar proportion of polyphosphate, in a pump dispenser having a walled dispensing chamber in which the dispensing chamber walls and parts of the pump dispenser that contact the dentifrice during storage and during dispensing thereof are of material(s) that is/are compatible with the triclosan and polyphosphate in the dentifrice and do(es) not cause excessive loss(es) of anti-plaque and anti-tartar properties of the dentifrice during storage thereof in and dispensing thereof from the container. The losses of anti-plaque activity are desirably held by the present invention to less than 25% on aging at room temperature and at elevated temperature, e.g., three weeks at 40° C., and such activity will preferably be maintained at such a level for at least a year at room temperature. Such stabilization of the triclosan (which is evidenced by such limited losses of anti-plaque activity) is effected by employing for dispenser parts plastics that are compatible with the triclosan, such as polyfluorocarbons, preferably of the polyfluoroethylene type, e.g., polytetrafluoroethylene, or polyvinyl compounds, preferably polyvinyl halides, e.g., polyvinyl chloride. However, an alternative technique is to include a stabilizing material in the dentifrice which material may be a terpene, e.g., limonene, or a flavor incorporating such a terpene or other stabilizer. Such stabilizing action may be inhibition of chemical reactions of the triclosan with the plastic or with other materials in the presence of the plastic, may be inhibition of sorption of the triclosan by the plastic, or may be another mechanism, unknown at the present. The described compositions preferably also include the previously mentioned fluoride and copolymer in such proportions as to be effective in their desired functions.

The invention will be readily understood from the description thereof in this specification, taken in conjunction with the drawing, in which.

Figure 1:
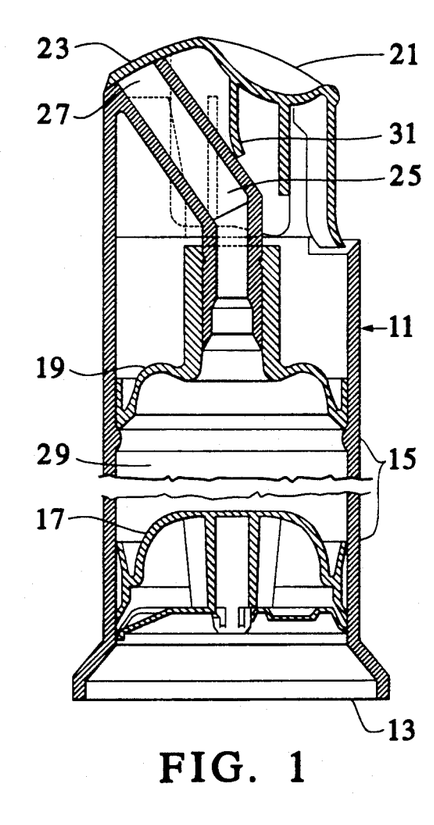
FIG. 1 is a central vertical sectional elevational view of a dispensing container of the finger actuatable pump type, shortened to omit some wall material, and containing dentifrice ready to be dispensed.

In FIG. 1 there is illustrated a pump dispenser of the type described in U.S. Pat. No. 4,776,496, which will be referred to as the Guala pump. For clarity, the contents of paste, gel or other viscous dentifrice are not illustrated in the drawing but it is to be understood that they occupy the volume between the floating piston and the outlet from the container. Dispenser 11 includes a base 13, cylindrical outer wall 15, floating compartment bottom 17, elastic or resilient membrane 19, actuator 21, which includes retractable nozzle cover portion 23, discharge conduit 25, and outlet nozzle 27. Numeral 29 represents the compartment in which the dentifrice is stored before discharge. In operation, depression of actuator 21 by thumb or finger pressure while the container is being hand held causes retraction of nozzle cover portion 23 and opens nozzle 27, while at the same time moving the nozzle, discharge conduit 25 and membrane 19 downwardly. Membrane 19, being elastic or resilient, is flattened somewhat by the downward motion and because floating bottom 17 is designed so that it can move only upwardly, dentifrice is discharged from compartment 29 through conduit 25 and nozzle 27. Upon release of the pressure against actuator 21 it returns to its initial position, due to the spring action of leaf spring part 31 and the conduit and nozzle return to their initial positions, as resilient membrane 19, with the mechanical pressure on it having been removed, also returns to its initial position. Atmospheric pressure (also called air pressure herein) moves bottom 17 upwardly a distance sufficient to compensate for the volume of dentifrice discharged. It will be noted that because bottom 17 and membrane 19 are similarly shaped the pump dispenser is capable of discharging substantially all the contents of the container (except for such portion which may fill conduit 25).

Figure 2:
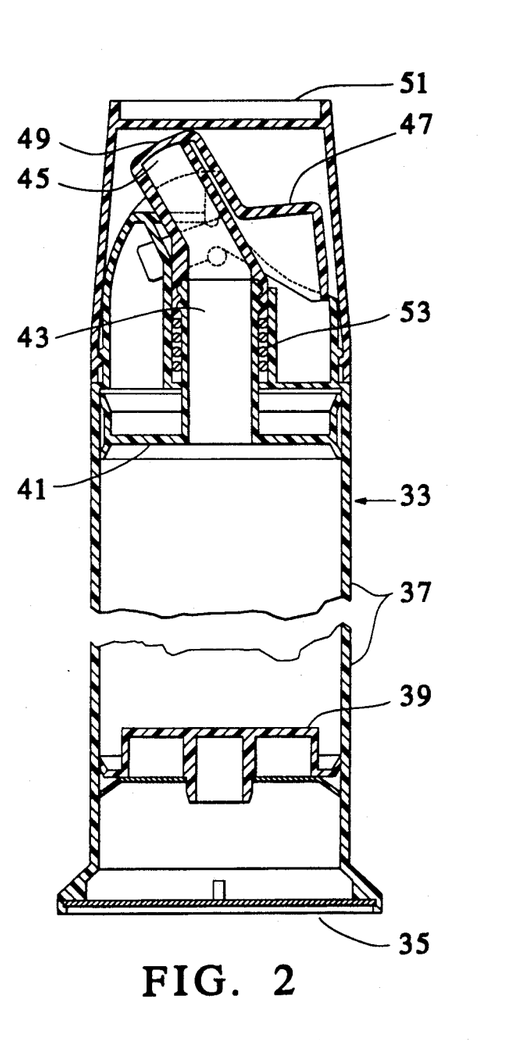
FIG. 2 is a central vertical sectional elevational view of another dispensing container, also of the finger actuatable pump type, but of a different construction, also containing dentifrice, but shown with a protective cover in place.

In FIG. 2 another type of dispenser for paste, gel or other viscous dentifrices is illustrated, which is like that described in U.S. Pat. No. 4,684,044, and which also resembles that of U.S. Pat. No. 4,691,847. Such dispenser will be referred to in this specification as the Realex pump. As in the description of the pump dispenser of FIG. 1, the contents of dentifrice are not illustrated in the drawing. Pump dispenser 33 comprises a base 35, cylindrical outer wall 37, floating piston compartment bottom 39 and pumping piston 41, which is connected with discharge conduit 43 and nozzle 45. Actuator 47 includes a nozzle cover portion 49. In the drawing a cap 51 is illustrated in place, protecting the upper portion of the pump dispenser and preventing unintentional depression of the actuator and discharge of contents. Operation of the Realex pump dispenser is essentially the same as that of the Guala dispenser. Cap 51 is removed and finger pressure is applied to actuator 47, which first causes nozzle cover portion 49 to be retracted, after which such pressure moves pumping piston 41 downwardly, together with discharge conduit 43 and nozzle 45, compressing helical spring 53. Such downward movement of the assembly forces dentifrice upwardly through conduit 43 and out nozzle 45 because floating piston 39 is incapable of downward motion. A measured amount of dentifrice is discharged if actuator 47 is pressed down to its limited bottommost position. Upon relaxation of pressure on the actuator, spring 53 returns the pumping piston, conduit and nozzle assembly to initial position and floating piston 39 moves upwardly, due to air pressure, a distance sufficient to compensate for the volume of dentifrice dispensed.

In the above descriptions of the packages of FIGS. 1 and 2 the terms "upwardly" and "downwardly" are used in a relative sense only and it will be apparent to the reader of this specification that dispensings of the packages' contents may be effected while the container is held in various orientations, including inverted positions.

The various internal parts of the pump dispensers that contact the dentifrice are preferably of plastic(s) that do not inactivate triclosan or polyphosphate, but the polyphosphate is sufficiently stable so that inactivation thereof in the dispensing container is not usually a serious problem. If it is not feasible to utilize plastics that have the necessary physical properties for the various contacting parts and still are compatible with triclosan other plastics may be employed, preferably such as adversely affect triclosan least, and preferably in such cases the toothpaste composition (or gel dentifrice) will include a stabilizing substance such as limonene or other operative terpene or flavor component. However, it is considered better to avoid employing any co-polyester polyether elastomers, such as have in the past been used for pumping membranes, which plastics appears to be especially active against triclosan in dentifrices. Instead, it may be preferred to utilize laminates which contain polyethylene terephthalate, ethylene vinyl alcohol or ethylene vinyl acetate, sandwiched between outer layers of polyethylene or some other such suitable plastic, with the total thickness often being in the range of 0.0005 to 0.01 inch, and with the inner layer being 5 to 50% of the thickness. Sometimes one or more of the layers may be metallized, as by aluminum or other suitable metal.

Because triclosan is to some extent photosensitive, it will sometimes be desirable for the pump dispensers of this invention to include containers, closures and caps which are coated or laminated with a chemical or physical light screening material, many of which are known, to prevent transmission to the dentifrice and to the triclosan therein of any inactivating radiation, e.g., ultraviolet light. Also, such containers may desirably be opaque to prevent such actinic radiation from inactivating the triclosan in the dentifrice.

The cause(s) of inactivation by plastics of triclosan in packaged dentifrices has/have not yet been established. Research to date has not pinpointed the mechanism responsible for losses of such desirable activity and so far test results do not conclusively point to either chemical reactions or physical absorptions. Tests of some oral preparations containing triclosan show that when they are aged in dispensing containers at room temperature, 38° C. and 49° C., for up to twelve weeks, there can be "excessive" losses (over 25% of the effect of the initial concentration of triclosan being lost) when such a preparation has been in contact with such container walls and parts of low density polyethylenes, high density polyethylenes, polyethylene terephthalates, polypropylenes, nylons, polyallomers and polymethylpentenes. Similarly, high losses result when such storage is in containers with inner walls or parts of co-polyester/polyether elastomers, such as those which had previously been employed in Guala pump membranes. In other experiments it was found that polyfluorocarbons and polyfluoroethylenes, such as polytetrafluoroethylenes, polyvinyl chlorides, polycarbonates and polysulfones did not absorb or react with excessive proportions of triclosan. However, polycarbonates and polysulfones are brittle and hence can be unsuitable for employment for some dispensing container parts. Polyvinyl chlorides can sometimes impart a foreign taste to dentifrices, and therefore might be avoided as a packaging material, except in cases where such taste is compatible with the taste of the flavoring employed. Thus, of all the polymeric plastic materials available, polyfluoroethylene is an especially satisfactory material for use in the present containers or packages, and does not seriously diminish the anti-plaque activity of triclosan. However, as was indicated previously, by incorporating in the oral compositions of suitable stabilizing compounds for triclosan, such as terpenes, of which limonene is representative, essential oils (which often contain terpenes) and other flavor components with similar "stabilizing" properties, one is able to reduce the activity losses of the triclosan when dentifrices containing it are in contact with containers or container parts made of the various mentioned polymeric plastics which are "stabilizable", so that excessive losses in anti-plaque activity do not occur. Therefore, one needs not be dependent on polyfluoroethylene as a dispenser material, providing that the dentifrice also contains a stabilizing proportion of terpene or other suitable "stabilizer". When such stabilizer is present in the oral compositions or when polyfluoroethylene (or polyvinyl chloride, polycarbonate or polysulfone) is the only polymeric plastic in contact with the oral composition, storage losses of anti-plaque activity are less than 25%, and preferably will be less than 10%, even after ambient to relatively high temperature storage, for example 20° to 40° C., for periods of time of several weeks to up to a year or more. It is considered that the most stable dentifrices are those which include a stabilizing proportion of terpene or other suitable stabilizer and also include contacting container parts of polyfluoroethylene (or any of the other unreactive plastics) only. Although the terpenes and essential oils are the primary stabilizers according to the present invention, other flavor components may also contribute to the stabilization of the anti-plaque material, either by interfering with any destabilizing chemical reaction or by inhibiting absorption of the triclosan by the plastic (or by other unknown mechanism). Thus, it has been theorized that some components of dentifrices that tend to solubilize triclosan can act to maintain it in the dentifrice and inhibit or prevent its migration into the plastic. On the other hand, it has also been theorized that such a solubilizing action could promote migration of the solubilized triclosan into the plastic. Because the issue has not been resolved applicants are not bound by either theory. Also, while it is desirable for the terpenes and other stabilizers to be flavor components, that is not necessary, and the stabilizer may be useful solely for stabilization.

Although it is preferred that the packages of this invention include internal walls and parts which come into contact with the packaged dentifrices that are of or are lined with synthetic organic polymeric plastic material, it is within the invention to utilize other solid (and/or film-forming) polymeric materials, whether or not they are synthetic, organic or even plastic. Thus, polyethylene glycols and methoxypolyethylene glycols, such as those of the Carbowax ® type, e.g., Carbowax 4,000 and Carbowax 6,000, may often be employed as lining materials in dispensers for dentifrices. Well known silicon polymers, such as siloxanes, and natural organic film-forming materials, such as gums, e.g., carrageenan, tragacanth, karaya, may also be useful as liners for the present pump dispensers. Additionally solid polymeric materials, such as cellulose, starches and derivatives thereof, may also be employable as liners and coatings for container materials where such contact the present triclosan-containing dentifrices.

The dentifrices of this invention are comprised of three classes of components, vehicle, polishing material and surfactant (or detergent). Triclosan is normally present in the vehicle of the packaged dentifrices, which vehicle usually comprises about 10 to 80%, preferably 50 to 80% (the figures are on a final composition basis) of the dentifrice. Of the vehicle, about 20 to 90% preferably 30 to 80%, will be water, about 20 to 80%, preferably 30 to 60%, will be humectant, such as glycerol, sorbitol, propylene glycol, polyethylene glycol or any suitable mixture thereof and 0.5 to 10%, preferably 1 to 5%, will be gelling agent, such as sodium carboxymethyl cellulose, Irish moss, iota carrageenan, calcium carrageenan, or hydroxyethyl cellulose or the like, including any suitable mixtures thereof. Although triclosan is essentially insoluble in water it is soluble or at least readily dispersible in the described dentifrice vehicle. The polishing material of the dentifrice will normally be from about 10 to 50%, preferably 15 to 25% thereof and such polishing material may be colloidal silica, precipitated silica, hydrated silica, sodium aluminosilicate, insoluble sodium metaphosphate, hydrated alumina, calcined alumina, dicalcium phosphate dihydrate, anhydrous dicalcium phosphate or calcium carbonate, or other known polishing agent, or any mixture thereof. The surfactants include anionic, nonionic, cationic and zwitterionic surfactants but often the employment of nonionic surfactant is avoided in the packaged dentifrices of this invention because of its adverse affect on triclosan, and the employments of cationic and zwitterionic surfactants are also often avoided because they tend to stain or darken the teeth. Thus, synthetic organic anionic surfactants, which are also detergents, are the preferred cleaning agents in the present dentifrices, and of these, sodium lauryl sulfate and other sodium higher alkyl sulfates of 10 to 18 carbon atoms in the alkyl groups thereof are preferred, although various other well known sulfated and sulfonated detergents, preferably of similar carbon chain lengths, may be substituted for them, at least in part. The surfactant or detergent content, usually anionic detergent content, is normally in the range of 0.2 to 10%, preferably 0.5 to 5%, and more preferably 1 to 3%.

In the packaged dentifrices there will very preferably also be present an effective anti-tartar (and anti-calculus) proportion of polyphosphate. Representative examples of the polyphosphate for the purpose of this description, include metaphosphates, such as sodium hexametaphosphate, polyphosphates, such as sodium tripolyphosphate, and pyrophosphates, such as tetrasodium pyrophosphate (which is most preferred), disodium diacid pyrophosphate and trisodiumonoacid pyrophosphate, the corresponding potassium salts, and the like. Such polyphosphates also include the linear molecularly dehydrated polyphosphate salts which are generally employed in the forms of their wholly or partially neutralized water soluble alkali metal (e.g., potassium and preferably sodium) or ammonium salts, and any mixtures thereof. In the present invention the polyphosphates are employed in the dentifrices in concentrations of 0.1 to 3% typically 0.5 to 3%. and more preferably 1.5 to 2.5%, e.g., about 2%. Particularly desirable are tetraalkali metal pyrophosphates, including mixtures thereof, such as tetrasodium pyrophosphate, tetrapotassium pyrophosphate and mixtures thereof.

To improve the anti-calculus and anti-tartar effectiveness of the dentifrice an inhibitor against enzymatic hydrolysis of the polyphosphate is desirably present. Such an agent is a fluorine ion source sufficient to supply 25 p.p.m. to 5,000 p.p.m., preferably 500 to 3,000 p.p.m. of fluorine ions (or fluoride ions) in the dentifrice.

Sources of fluorine ions or fluorine-providing components for inhibiting the actions of acid phosphatase and pyrophosphatase enzymes on polyphosphate (and thereby for increasing anti-tartar and anti-calculus effectiveness of the polyphosphate) in the present dentifrices are well known in the art, and usually also function as tooth hardeners and anti-caries agents. These compounds may be slightly soluble in water or may be fully water soluble. They are characterized by their ability to release fluorine ions in water and by their relative inertness toward other compounds of the dentifrices. Among these materials are inorganic fluoride salts, such as soluble alkali metal and alkaline earth metal salts, e.g., sodium fluoride, potassium fluoride, ammonium fluoride, calcium fluoride, copper fluorides, such as cuprous fluoride, zinc fluoride, barium fluoride, tin fluoride, sodium fluorosilicate, ammonium fluorosilicate, sodium fluorozirconate, ammonium fluorozirconate, sodium monofluorophosphate, aluminum mono- and difluorophosphates, and fluorinated sodium calcium pyrophosphate. Alkali metal and tin fluorides, such as sodium and stannous fluorides, sodium monofluorophosphate (MFP®) and mixtures thereof are preferred.

The amount of fluorine-providing compound in the present oral preparations is dependent to some extent upon the type of compound, its solubility, and the types of oral preparations, but it should be a non-toxic amount, generally in the range of about 0.005 to about 3.0% and preferably in the range of 0.05 to 1% in the dentifrice.

Typically, in the cases of alkali metal fluorides, this component is present in an amount up to about 2% by weight, e.g., 0.05 to 2%, based on the weight of the preparation, and preferably in the range of about 0.1 to 1%, e.g., about 0.33%. In the case of sodium monofluorophosphate, the compound may be present in an amount of about 0.1 to 6%, typically 0.5 to 1%, e.g., about 0.76% or 0.8%.

In another preferred aspect of this invention the dentifrice comprises an agent that is effective to enhance the antibacterial and anti-plaque effect of the triclosan. Such antibacterial enhancing agent (AEA) is preferably of an average molecular weight in the range of about 1,000 to about 1,000,000 and desirably contains a functional group which enhances the antibacterial effect and an organic group which enhances retention of such antibacterial effect.

The AEA is preferably a synthetic anionic polymeric polycarboxylate which is also an inhibitor of alkaline phosphatase enzyme. In U.S. Pat. No. 4,627,977 (Gaffar et al.) there is described the use of polycarboxylates for inhibiting salivary hydrolysis of pyrophosphate anticalculus agents in combination with a compound which acts as a source of fluoride ion. It is to be understood that the synthetic anionic polymeric polycarboxylates so disclosed, when containing or modified to contain the retention-enhancing group mentioned above, are operative as AEA's in the compositions and articles of the invention, and are in fact, components of preferred embodiments thereof.

The mentioned synthetic anionic polymeric polycarboxylates are often employed in the form of their free acids or preferably partially or more preferably fully neutralized water soluble or water swellable (hydratable, gel/forming) alkali metal (e.g., potassium and preferably sodium) or ammonium salts. Preferred are 1:4 to 4:1 copolymers of maleic anhydride or equivalent acid with another polymerizable ethylenically unsaturated monomer, preferably methyl vinyl ether/maleic anhydride having a molecular weight (M.W.) of about 30,000 to about 1,000,000. These copolymers are available from GAF Corporation as, for example, Gantrez® AN 139 (M.W.=500,000), AN 119 (M.W.=250,000); and preferably S-97 Pharmaceutical Grade (M.W.=70,000).

Other polymeric polycarboxylates which are operative as AEA's and contain or are modified to contain retention-enhancing groups include those disclosed in U.S. Pat. No. 3,956,480, such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrollidone.

Additional operative polymeric polycarboxylates are disclosed in U.S. Pat. Nos. 4,138,477 and 4,183,914, which contain or may be modified to contain retention-enhancing groups. These include copolymers of maleic anhydride with styrene, isobutylene or ethyl vinyl ether, polyacrylic, polyitaconic and polymaleic acids, and sulfoacrylic oligomers of a M.W. as low as 1,000, which is available as Uniroyal ND-2.

Other suitable anionic polymers that may be employed as AEA's are described in greater detail in U.S. Pat. No. 3,956,480 and in Ser. No. 07/398,605, both of which are incorporated herein by reference. The percentage of such AEA(s) in the described compositions will normally be in the range of 0.2 to 5%, preferably being 0.5 to 4% and more preferably 1 to 3%, e.g., 2%

In dentifrice compositions the effective amount of triclosan will normally be in the range of 0.1 to 1.0%, more preferably 0.2 to 0.5 or 0.6%, e.g., about 0.3%, and often not exceeding 0.8% because of possible mouth numbing effects at higher concentrations, and not being less than indicated to avoid ineffectiveness against plaque. Preferably the dispensed dentifrices will contain proportions of triclosan within the given ranges but when the initial concentration thereof is within the given range a loss of up to 25% will be acceptable and such dispensed compositions are within the scope of the invention and are effective.

For stabilized dentifrices that are to be packaged in containers containing plastic walls or other parts, wherein the plastics are those which are "reactive" with triclosan, 0.01 to 2% of terpene(s) or stabilizer(s), preferably 0.05 to 1% and more preferably 0.1 to 0.5% will be present in the dentifrice. Such stabilizers may be present in a suitable flavoring agent for the dentifrice, if desired (and it often is), and will be at least 5% of the flavor, preferably at least 10%, more preferably at least 25% and most preferably at least 50%.

The various plastics that were previously described as the components of container and/or dispenser parts have been described only briefly because it is considered that their chemical natures and degrees of polymerization are well known, so detailing thereof is unnecessary in this specification. If further details are wanted reference may be made to Modern Plastics Encyclopedia, which is published on an annual basis by McGraw-Hill Inc., New York, N.Y.

The stabilizer terpenes, which term, for the purpose of this specification, includes the terpene hydrocarbons and oxygenated derivatives thereof, include such compounds as dl-limonene, menthol, diterpenes, polyterpenes and derivatives thereof, many of which are found in various essential oils and other flavors. In addition to being useful as stabilizers for triclosan they often contribute desirable flavors to the present dentifrices. Of the terpenes and their derivatives it is considered that limonene best balances these properties, although other terpenes, including those which are not flavors, are also useful, as are other emulsifiable lipophilic essential oils and flavoring agents which contain stabilizing components.

For other details of formulations, components, adjuvants, manufacturings and uses, see the patents and applications previously mentioned in this specification, which are hereby incorporated by reference, as are text and periodical references.

Manufacture of the described dentifrices is by any of various standard techniques for producing such classes of compositions. Referring to specific examples for simplicity, the triclosan is dispersed and/or dissolved in the vehicle portion of the dentifrice and the terpene is present in the flavoring agent. To make the dentifrice, the vehicle is prepared containing glycerol, sorbitol, and propylene glycol, gelling agents, triclosan and suitable adjuvants (including Gantrez S-97), and the vehicle and aqueous anionic detergent (preferably sodium lauryl sulfate or a mixture of sodium lauryl sulfate and sodium methyl cocoyl taurate) solution are mixed, followed by blending in of the polishing agent component, which may include the polyphosphate and fluoride, with the pre-mix. Finally, flavoring agent, including terpene, desirably dissolved in ethanol, is admixed and the pH is adjusted.

In packaging of the dentifrice in the dispensing container it will be desirable to avoid contacting of the dentifrice with plastic parts of co-polyester/polyether elastomer and it will also be desirable to avoid contacting of any compositions not containing stabilizing agent (such as terpene or flavor containing it) with plastic parts made of those plastics previously listed in this specification as reactive with triclosan and other such antibacterial and anti-plaque compounds. It will be especially important to avoid the mentioned plastic parts for holding tanks or any other containers, piping, pumps or equipment, in which the triclosan or the dentifrice containing it may be held for any appreciable length of time or held for shorter lengths of time at elevated temperatures.

Even when the packaged compositions of this invention are prepared and contacts of the dentifrices containing triclosan with the reactant plastics are avoided it will still be desirable to minimize exposures of such packaged dentifrices to heat and to light, both of which have been found to accelerate losses of anti-plaque activity. Thus, the invented compositions are preferably stored and packaged in opaque dispensers or ones that filter out actinic light, at a temperature in the range of 10° to 38° C. Otherwise, the packaged dentifrices may be stored and used in normal manner and the desirable anti-plaque and anti-tartar effects thereof will be obtained. Such effects have been verified by laboratory testing and by evaluations of the teeth of volunteers serving on human panels, who employed the various packaged dentifrices and controls as directed. Significant improvements in anti-plaque activities of the compositions of this invention packaged in the described pump dispensers are observable compared to control dentifrices similarly packaged but wherein the dispenser includes plastic parts that are "reactive" with the triclosan and which do not contain stabilizing agent in the dentifrice. Such improvements are also found when dispensers made of "reactive" plastics (but not co-polyester/polyether elastomers) are employed with dentifrices containing terpenes and are compared to controls in which the dentifrices contain no terpenes and no flavoring agents.

The following examples illustrate but do not limit the invention. Unless otherwise indicated, all percentages and proportions in these examples, the specification and the appended claims are by weight, and all temperatures are in ° C.

EXAMPLE 1

| Component | Percent |
| --- | --- |
| Propylene glycol | 10.00 |
| Iota carrageenan | 0.75 |
| Sodium fluoride | 0.33 |
| Sorbitol (70% aqueous solution) | 30.00 |
| Sodium saccharin | 0.30 |
| Titanium dioxide | 0.50 |
| Sodium hydroxide (50% aqueous solution) | 0.80 |
| ⁻Luviform TM (35% aqueous solution) | 4.76 |
| ⁻⁻Zeodent TM 113 | 20.00 |
| ⁻⁻⁻Sident TM 22S | 2.00 |
| Sodium lauryl sulfate (94% active) | 1.60 |
| *Flavor | 0.95 |
| **Triclosan | 0.30 |
| | 100.00 |

⁻35% Aqueous solution of polyvinyl methyl ether/maleic anhydride copolymer (BASF Corp.)
⁻⁻Silica polishing agent (J. M. Huber Corp.)
⁻⁻⁻Silica thickening agent (Degussa Co.)
*Contains at least 25% of terpenes. e.g., limonene
**Irgasan ® DP 300. mf'd. by CIBA-GEIGY A dentifrice of the above formulation is made in normal manner and is employed as a medium for testing the stability of triclosan when the dentifrice containing it is exposed to different plastics which are employed as materials of dispensing containers or parts thereof in which or in contact with which such dentifrices are stored and dispensed. The plastics for the tests are Pibiflex TM 46, made by Inmont, and Arnitel TM 460 EM, mf'd. by AKZO, which are plastics that are employed as the membranes or bellows of a pump dispenser, as illustrated in FIG. 1. Six samples of plastics are tested, three of each of the mentioned plastics, with each of the three being treated with a different mold release agent (to determine whether the nature of the release agent is relevant to the problem of triclosan stability in contact with plastics during storage). The release agents are Silicone Master TM (5% silicone oil and 95% polypropylene), Silicone Master plus Silicone Oil (with extra silicone oil) and Armid O Master TM (5% oleyl amide and 95% polypropylene), respectively. After two weeks storage of the test samples in contact with the dentifrice at different temperatures (room temperature, 38° C. and 49° C.), the dentifrice samples are removed from the plastic container materials and the plastics are washed with water and immersed in methanol to dissolve any triclosan which might have been taken up by them during storage. The methanol washings are collected and are analyzed, using high performance liquid chromatrography. It is found that essentially the same types of absorptions of triclosan take place with the different membrane materials and although there are variations between them and such are somewhat dependent on the release agents employed, the results are essentially the same in all cases. The co-polyester/polyether elastomers are found to absorb significant percentages of triclosan from the dentifrice, which results are confirmable when the co-polyester/polyether elastomers are used as bellows materials in pump dispensers containing the described dentifrice and other dentifrices within the invention. Accordingly, it is considered undesirable to employ co-polyester/polyether elastomers in contact with the present dentifrices and that is even so when the dentifrices contain terpenes or contain flavoring materials which include terpenes (which are present in the flavoring of the dentifrice formulation), to the extent of at least 0.1% of the dentifrice.

When the tests are repeated, using Guala pump dispensers as containers for the dentifrices, with co-polyester/polyether elastomer membranes of Arnitel TM, the losses of triclosan are also unacceptable but when the co-polyester/polyether elastomer is replaced by others of the acceptable plastics, e.g., Teflon ® polyfluoroethylene, the triclosan activity is improved to within acceptable limits. Also, other plastic parts of such pump dispensers, such as polypropylene inner walls thereof, are not found to absorb excessive amounts of triclosan and do not seriously decrease the anti-plaque activity of the dentifrice, apparently due to the presence of terpenes in the flavoring agent of the contained dentifrice.

A panel test is run, involving at least ten human subjects, who employ the dentifrice of this example, dispensed from polyethylene terephthalate- and polyethylene-lined dispensing containers, in twice-a-day brushings for one month, during which time plaque evaluations of the subjects' teeth are made by trained observers. The test results establish that the dentifrice composition has a definite anti-plaque activity and also prove that the triclosan has not been unacceptably inactivated, and still is present in an effective antibacterial and anti-plaque proportion in the dentifrice. Similar good results are obtainable when pump dispensers like that illustrated in FIG. 2 are employed and comprise dispensing containers including walls and other parts of high and low density polyethylenes, polypropylenes, polyallomers, nylons, acrylics, polyfluorocarbons, polyvinyl halides, polycarbonates, and/or polysulfones. Such stability of the triclosan is also obtainable when the terpene content is decreased or when terpenes are omitted, providing that the plastic parts are of polytetrafluoroethylene, polyvinyl chloride, polycarbonate and/or polysulfone.

The dentifrice formula will desirably also include 1.5 to 2.5%, e.g., 2%, of a polyphosphate (sodium hexametaphosphate, tetrasodium pyrophosphate, or sodium tripolyphosphate, or a mixture thereof), preferably the pyrophosphate, to give the dentifrice desired anti-tartar action. It is also highly preferable for such compositions to contain a fluorine ion releasing compound, such as 0.3% of sodium fluoride or 0.8% of sodium monofluorophosphate, and 2% of polyvinyl methyl ether/maleic anhydride copolymer, for their functions that were previously mentioned herein. Additions of such materials to the formula is compensated for by decreasing the water content accordingly.

EXAMPLE 2

| Component | Percent |
| --- | --- |
| Glycerol | 7.00 |
| Propylene glycol | 3.00 |
| Iota carrageenan | 0.75 |
| Sorbitol (70%) | 30.00 |
| Sodium saccharin | 0.30 |
| Sodium fluoride | 0.33 |
| Titanium dioxide | 0.50 |
| Gantrez S-97 (13% solution) | 15.00 |
| Deionized water | 16.07 |
| Sodium hydroxide (50% aqueous solution) | 0.80 |
| ***Zeodent 113 | 20.00 |
| *Sylodent ® 15 | 3.00 |
| Flavoring agent (containing at least 25% of terpenes) | 0.95 |
| Sodium lauryl sulfate | 2.00 |
| Triclosan | 0.30 |
| | 100.00 |

***Polishing agent (J. M. Huber Corp.)
*Silica thickening agent (W. R. Grace Corp.)

A toothpaste of the above formula is made and is stored in Guala ™ pump dispensers having bellows membranes of the Arnitel type. The dentifrice is also filled into dispensing containers having laminated walls of polyethylene terephthalate in the interior of the laminate, which contain the dentifrice. The dentifrices are aged at 5° C., 25° C., and 39° C., for two, four and six weeks. After such aging periods, the dentifrices are dispensed at the rate of about 1.5 grams per day and at weekly intervals the triclosan contents of the dispensed dentifrice are determined by analyses. In the case of the Guala pump dispenser with Arnitel membrane the dispensed dentifrice loses about 27% of the triclosan, which is excessive and objectionable. The loss is about constant, regardless of storage temperature or time of storage, which can be explained by theorizing that the triclosan is absorbed by the pump membrane, with which it is in contact prior to dispensing. Such membrane is of a co-polyester/polyether elastomer, which class of plastics is to be avoided as a container material or as a part in a pump dispenser for dentifrices containing triclosan. However, when the elastomeric co-polyester/polyether membrane is replaced by one made of any of the previously mentioned acceptable plastics, such as polyethylene terephthalate, which can serve as membrane materials in modified pump dispensers (modified to compensate for different properties of such plastics) or as pumping pistons in Realex type pumps triclosan stability is increased and the dispensed composition is satisfactory and effective as an anti-plaque toothpaste. It is notable that the Realex pump design does not require an elastic or flexible plastic component, and on that basis such pump may be considered superior in design to the Guala pump because it allows a greater selection of plastics for the pumping piston and so better allows one to avoid uses of any objectionable plastics.

Incorporation of tetrasodium pyrophosphate, sodium tripolyphosphate or sodium hexametaphosphate, as in Example 1, (preferably 2% of the pyrophosphate) makes the dentifrice anti-tartar, as well as anti-plaque.

Gel dentifrice formulations in such pump dispensers behave similarly to toothpastes with respect to triclosan stability after storage and on dispensing.

In similar tests, using polyethylene terephthalate-lined dispensing containers little loss (less than 5%) of triclosan is noted, indicating that the presence of the terpenes (0.1% or more of the composition), including limonene, in the flavoring agent or as the flavoring agent, prevents loss of the triclosan or inactivation thereof. When polyfluoroethylene-lined tubes are employed there is little loss of triclosan, even when the flavoring agent is omitted from the dentifrice composition and such is also the case when polyvinyl chloride is employed as a primary material in contact with the dentifrice and or when polysulfone or polycarbonate package parts are in contact with such dentifrice.

In the above formulas the polishing systems are siliceous rather than being based on alumina. When the polishing agents are changed to aluminas, the triclosan stability problems previously mentioned as having been noted with some plastics are decreased, but they still exist. Also, the presences of terpenes in the dentifrices promote triclosan stability, as such presences do in similar dentifrice compositions based on siliceous polishing agents.

EXAMPLE 3

The dentifrices of the foregoing examples may be varied in composition ±10% and ±25% for the various components thereof, providing that such percentages are not outside ranges given elsewhere in this specification, and operative and effective anti-plaque and anti-tartar products are obtainable, which are dispensable in effective anti-plaque and anti-tartar state from the mentioned dispensing containers that are made of compatible plastics. Such products also will behave in similar manners, with the triclosan anti-plaque agent being sufficiently stable in the presence of polyfluoroethylene, polyvinyl chloride, polycarbonate and polysulfone packaging or package component materials, even when no flavoring agent and no terpenes are present in the dentifrices, and being stable in the presence of polyethylenes, polypropylenes, polyethylene terephthalates, polymethylmethacrylates, polyallomers, nylons and polymethylpentenes, as package or component materials, when a stabilizing terpene, such as limonene, or a stabilizing flavor component is present in the dentifrice. The packaged dentifrices of this example that contain polyphosphate, source of fluorine ions and AEA are also of effective anti-tartar, anti-calculus, anti-caries, tooth hardening and stabilizing (of the polyphosphate against enzymatic action) properties. When the AEA materials and fluoride are omitted the polyphosphate's anti-tartar and anti-calculi properties can be adversely affected by enzymatic action of the saliva but will still be present. As with the other packaged dentifrices and mouthwashes previously discussed, because of excessive absorption or other adverse action with respect to triclosan by co-polyester/polyether and other such elastomers, uses of such materials will preferably be avoided.

EXAMPLE 4

Dentifrices of the formulas of Examples 1 and 2 are made and are dispensed after one month's storage at 30° C., from containers lined with polyethylene, in one case, and polyethylene terephthalate, in another, onto bristled toothbrushes. The amounts of toothpaste on the toothbrushes are in the range of 0.8 to 2.0 grams with 1 to 1.5 g. being preferred. When 1.5 g. is dispensed the active triclosan in the dentifrice on the brush is about four milligrams (with only 10% of the triclosan being inactivated). When storage is for a longer time or at a higher temperature or with a more destabilizing plastic in contact with the dentifrice during storage the packaged dentifrices can contain about 3.5 mg. of triclosan in the 1.5 g. on the brush.

The described dispensed dentifrices are employed to brush the teeth, with typically about 0.8 to 2 g. being dispensed onto toothbrushes for each brushing. Brushings are twice a day, morning and night, one minute at a time, for four weeks, after which definite improvement in anti-plaque action is apparent, compared to a control dentifrice that contains no triclosan, and when polyphosphate is also present anti-tartar effects are also noticeable. Improvement in anti-plaque action is also visible, compared to an unflavored control (containing no terpene) that contains triclosan which is dispensed from polyethylene and polyethylene terephthalate lined containers.

For more details about the pump dispensers, materials of construction thereof and dentifrice composition components of the invention, if desired, please see the previously mentioned or referred to patents, applications, texts, bulletins and/or articles, which are hereby incorporated herein by reference.

The invention has been described with respect to various examples, illustrations and embodiments thereof but is not to be limited to these because it is evident that one of skill in the art, with the present specification before him/her, will be able to utilize substitutes and equivalents without departing from the invention.

What is claimed is:

1. An article comprising a hand holdable, finger actuated, floating piston pump dispensing container having solid polyethylene or polyethylene terephthalate polymeric material in contact with a dentifrice composition in the container, which composition comprises an effective antibacterial antiplaque proportion of a substantially water insoluble non-cationic halogenated diphenylether antibacterial antiplaque agent, at least about 25% of which has been found to be lost after twelve weeks storage at room temperature in said container, and a stabilizing terpene to make said polymeric material compatible with said agent in the presence of the oral composition whereby said loss is prevented and the dispensed composition contains more than about 75% of its initial content of said agent.

2. An article according to claim 1 wherein the dentifrice is in paste or gel form and further contains an effective anti-tartar proportion of linear molecularly dehydrated polyphosphate.

3. An article, according to claim 1 in which the dentifrice comprises 0.1 to 1% of triclosan.

4. An article, according to claim 3 in which the dentifrice comprises 0.1 to 3% of linear molecularly dehydrated polyphosphate.

5. An article, according to claim 1 in which the dentifrice comprises a vehicle, a polishing agent, and the pump dispenser comprises a walled tube, a pumping end on such tube, communicating with a discharge element and movable with respect to the tube, and a floating end on the tube, movable by air pressure toward the pumping end but not movable in the opposite direction.

6. An article according to claim 5 in which the dentifrice comprises 0.2 to 0.8% of triclosan, 0.5 to 3% of polyphosphate, 0.005 to 3% of a source of fluorine ions and 0.2 to 5% of synthetic anionic polymeric polycarboxylate, and the pump dispenser comprises a walled cylindrical tube, a dispensing nozzle communicating with the interior of the tube through a pumping piston in the tube, and a floating piston in the tube, with the pistons and the tube contacting the dentifrice.

7. An article according to claim 5 wherein the pump dispenser parts that contact the dentifrice during storage and dispensing of the dentifrice comprise polyethylene.

8. An article according to claim 2 in which the dentifrice comprises a stabilizing proportion of a terpene which stabilizes the triclosan in the presence of said polymeric material.

9. An article according to claim 8 in which the dentifrice comprises 0.01 to 2% of stabilizing terpene(s) and the contacting dispensing container parts are of polyethylene.

10. An article according to claim 9 in which the dentifrice comprises 0.1 to 1% of triclosan, 0.1 to 3% of polyphosphate, 0.05 to 1% of a source of fluorine ions, 0.2 to 5% of synthetic anionic polymeric polycarboxylate and 0.05 to 1% of stabilizing terpene(s).

11. An article according to claim 10 in which the dentifrice comprises 0.2 to 0.8% of triclosan, 1.5 to 2.5% of tetrasodium pyrophosphate, sodium tripolyphosphate or sodium hexametaphosphate or any mixture thereof, 0.1 to 1% of sodium fluoride or sodium monofluorophosphate or mixture thereof, 0.5 to 4% of polyvinyl methyl ether/maleic anhydride copolymer, and 0.1 to 0.5% of stabilizing terpene(s).

12. An article according to claim 6 in which the dentifrice comprises 0.2 to 0.5% of triclosan, 1.5 to 2.5% of tetrasodium pyrophosphate, sodium tripolyphosphate or sodium hexametaphosphate or any mixture thereof, 0.1 to 1% of sodium fluoride or sodium monofluorophosphate or mixture thereof, 0.5 to 4% of polyvinyl methyl ether/maleic anhydride copolymer and 0.1 to 0.5% of limonene.

13. An article according to claim 12 in which the dentifrice comprises about 0.3% of triclosan, about 2% of tetrasodium pyrophosphate, about 0.3% of sodium fluoride, and about 2% of polyvinyl methyl ether/maleic anhydride copolymer, and in which the parts of the container that contact the dentifrice during storage or during dispensing comprise polyethylene.

14. An article according to claim 1 in which the pump dispenser comprises a cylindrically walled container, an upwardly only movable floating piston compartment bottom and a pressure piston compartment top, which define a compartment of changeable volume for the dentifrice, a conduit and a nozzle which communicate with the compartment and facilitate the discharge of dentifrice from it when that is desired, an actuator for applying finger pressure to the pumping piston to move it downwardly to discharge dentifrice from the compartment through the conduit and nozzle, when desired, and spring means to return the pumping piston to initial position after discharge of dentifrice from the container, without sucking back contents from the conduit into said compartment.

15. An article according to claim 5 wherein the pumping piston is of a laminate of outer layers of polyethylene with polyethylene terephthalate or inner ethylene vinyl alcohol.

16. An article according to claim 4 wherein the pumping piston is of a laminate of outer layers of polyethylene with polyethylene terephthalates or inner ethylene vinyl alcohol layers.

17. An article comprising a hand holdable finger actuated, floating piston pump container dispenser having solid destabilizing polyethylene or polyethylene terephthalate polymeric material in contact with a viscous anti-plaque, anti-tartar dentifrice in the dispenser, which dentifrice comprises an effective anti-plaque proportion of a halogenated diphenyl ether, an effective anti-tartar proportion of polyphosphate antitartar agent, and a stabilizing proportion of a terpene which stabilizes the halogenated diphenyl ether in the presence of said destabilizing material.

18. An article according to claim 17 wherein said destabilizing material comprises polyethylene, said halogenated diphenyl ether comprises triclosan and said terpene comprises limonene and said polyphosphate comprises tetrasodium or tetrapotassium pyrophosphate or a mixture thereof.

19. An article according to claim 1 wherein the stabilizing terpene is not a component of a flavoring agent.

20. An article according to claim 17 wherein the stabilizing terpene is not a component of a flavoring agent.

* * * * *